Figure 1:
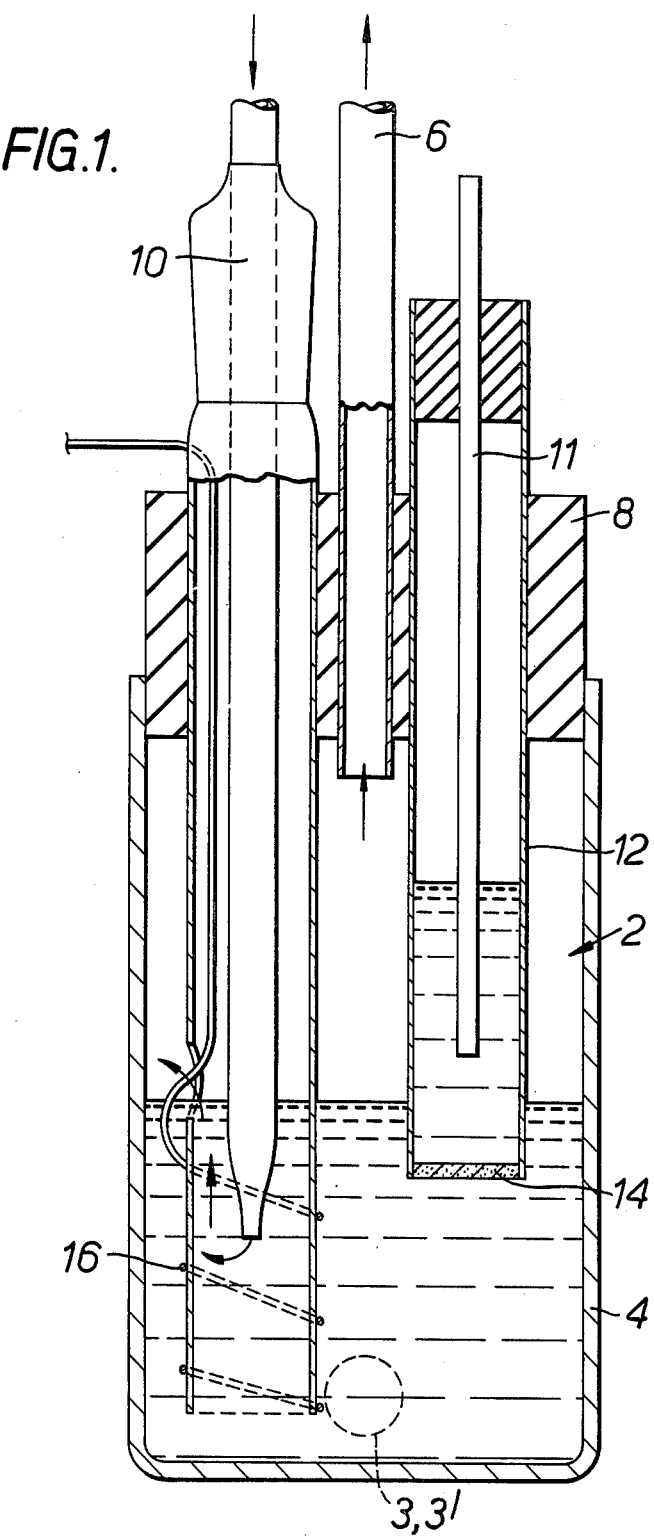

United States Patent [19]
Jenkins et al.

[11] 3,984,204
[45] Oct. 5, 1976

[54] GAS MONITORS

[75] Inventors: Rhys Haydn Jenkins, Swansea; Hugh John Boniface, Glamorgan, both of Wales

[73] Assignee: British Steel Corporation, London, England

[22] Filed: Apr. 14, 1975

[21] Appl. No.: 567,802

[52] U.S. Cl. .............................. 23/232 E; 23/254 E; 23/255 E; 324/29; 324/71 R
[51] Int. Cl.[2] ................. G01N 21/24; G01N 27/44; G01N 31/22
[58] Field of Search ........... 23/232 E, 232 R, 254 E, 23/255 E; 204/1 K, 1 F, 195 T; 356/180, 184

[56] References Cited
UNITED STATES PATENTS

| | | | |
|---|---|---|---|
| 2,949,345 | 8/1960 | Clauss | 23/232 E |
| 3,567,392 | 3/1971 | Schulze | 23/232 R |
| 3,723,062 | 3/1973 | Dahms | 204/195 T |
| 3,897,315 | 7/1975 | Riseman et al. | 204/1 F |

*Primary Examiner*—Robert M. Reese
*Attorney, Agent, or Firm*—Brisebois & Kruger

[57] ABSTRACT

A method for monitoring the toxic constituent of an ambient gas e.g. sulphur dioxide in air involves bringing the gas into contact with a solution containing one component in which the gas is soluble and an indicator having optical transmission characteristics responsive to the quantity of the constituent in solution. An electric current is then passed through a second component which is electrolysed to neutralise the solution and restore the transmission characteristics of the indicator to a datum, the quantity of current passed being representative of a change in transmission characteristics from the datum and therefore in the case of the concentration of the toxic constituent where sulphur dioxide in air is to be monitored the air is bubbled through water in which the sulphur dioxide dissolves. The water contains hydrogen peroxide to convert the sulphur dioxide in solution to sulphuric acid which is effective to change the color or optical density of a pH responsive indicator such as methyl orange. The second component in this case is a suitable electrolyte which can be electrolysed to form a base effective to neutralise the acid so as to maintain the indicator at the color or optical density level selected as the datum. Such an electrolyte is sodium chloride which forms sodium hydroxide as a base.

22 Claims, 3 Drawing Figures

GAS MONITORS

This invention relates to the assessment of a toxic constituent of an ambient gas and is particularly concerned with the assessment of the sulphur dioxide content of air.

Sulphur dioxide gas is recognised as an undesirable constituent in a working air environment. In relatively low concentrations the sulphur dioxide acts as an irritant whereas in higher concentrations it becomes progressively more toxic. Any working environment liable to contamination by sulphur dioxide must accordingly be carefully monitored to give adequate warning when contamination reaches an intolerable level. A similar problem arises in the case of air liable to contamination by carbon monoxide.

A number of methods have been proposed for monitoring air or other ambient gases liable to contamination by, for example, sulphur dioxide. In general these methods comprise bubbling the air through a sample of liquid in which the sulphur dioxide is soluble and subsequently subjecting the sample to analysis in order to assess the quantity of sulphur dioxide gas which has gone into solution.

One major disadvantage of such prior methods is that both the sampling and the subsequent analysis cover a time span involving a considerable time delay, between the onset of or increase in contamination and the conclusion of analysis. In steelworks in particular where large quantities of sulphur dioxide may be generated over a relatively short period, the delay inherent in conventional monitoring methods may prevent a rapid increase in contamination level being indicated in good time.

According to one aspect of the present invention, a method for monitoring the toxic constituent of an ambient gas comprises bringing the gas into contact with a liquid having one component in which the toxic constituent is selectively soluble together with an indicator having optical transmission characteristics responsive to the quantity of the constituent in solution, passing an electric current representative of a change in transmission characteristics from a datum through a second component which is arranged to electrolyse so as to neutralise the solution and thereby tend to restore the transmission characteristics of the indicator to the datum.

By maintaining the transmission characteristics at the datum, the electrolytic current passed through the liquid is indicative of incremental changes in dissolved toxic gas. Accordingly continuous monitoring of electrolytic titration current permits the concentration of toxic gas to be continuously assessed substantially without time delay.

In the case where the sulphur dioxide content of air is to be assessed, the air is bubbled through water in which the sulphur dioxide is selectively soluble. Preferably the water contains an oxidising agent such as hydrogen peroxide which converts the sulphur dioxide in solution to sulphuric acid which is effective to change the colour or optical density of a pH responsive indicator such as methyl orange.

In this case the water contains also any suitable electrolyte which can be arranged to produce a base effective to neutralise the acid so as to maintain the indicator at the colour or optical density level selected as the datum. A convenient electrolyte is sodium chloride which is electrolysed by the titration current to sodium hydroxide and chlorine. The volume surrounding the anode at which the chlorine or corresponding electrolytic product is evolved, is separated from the remaining volume of liquid by a semi-permeable membrane. This membrane prevents the chlorine or chlorine compounds interfering with the titration between sulphur dioxide in solution and the base generated at the cathode. Perferably the anode is of a material such as silver which reacts with evolved chlorine to form a stable and inert compound.

Conveniently the indicator datum is selected to produce the greatest change in colour or other transmission characteristics for a given change in acid concentration. In the case of methyl orange the liquid is preferably maintained at a pH lying between 3.9 and 4.0 so that the titration current is zero at this level.

The titration current may be controlled in response to an out of balance signal between the outputs of two photoelectric devices respectively arranged to receive light beams passing through and bypassing the liquid. Matched optical e.g. interference filters may be placed in the paths of the two beams in order to increase sensitivity to colour changes in the indicator.

Figure 2:
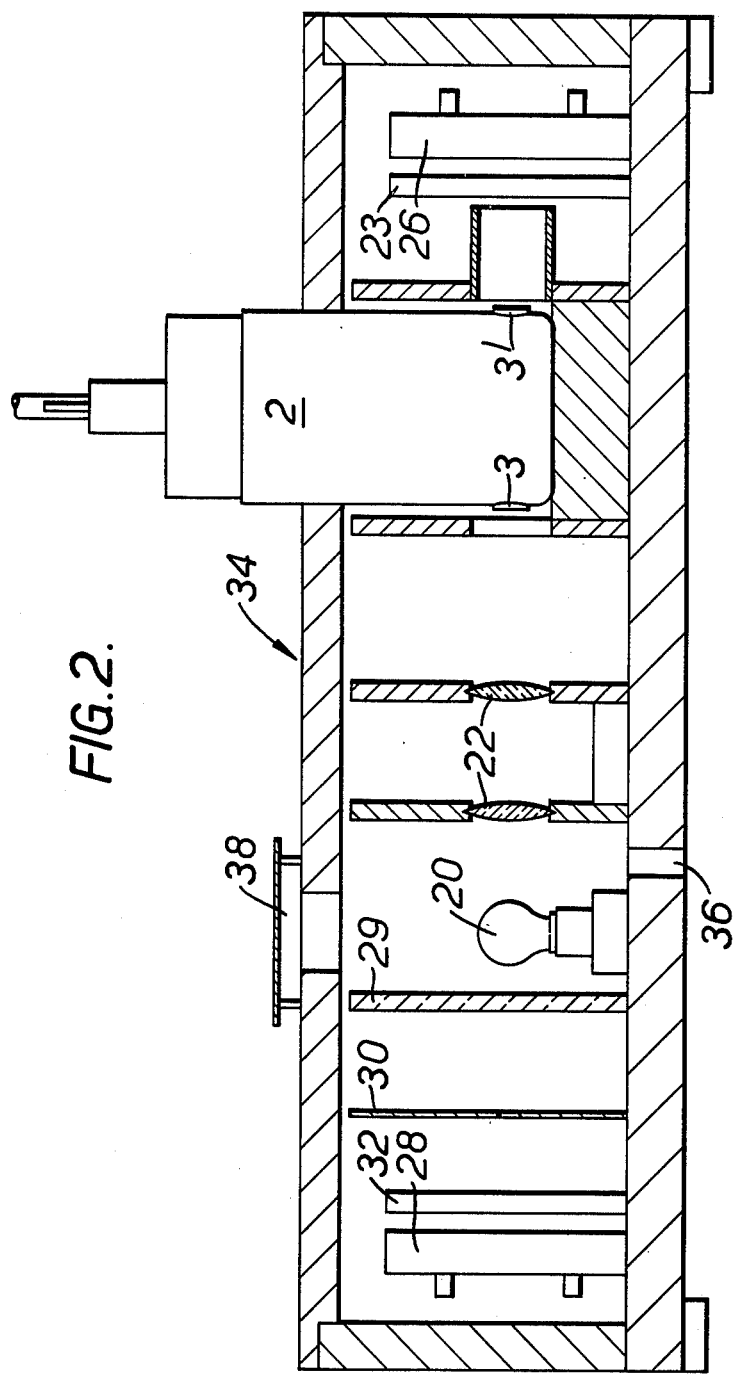
Figure 3:
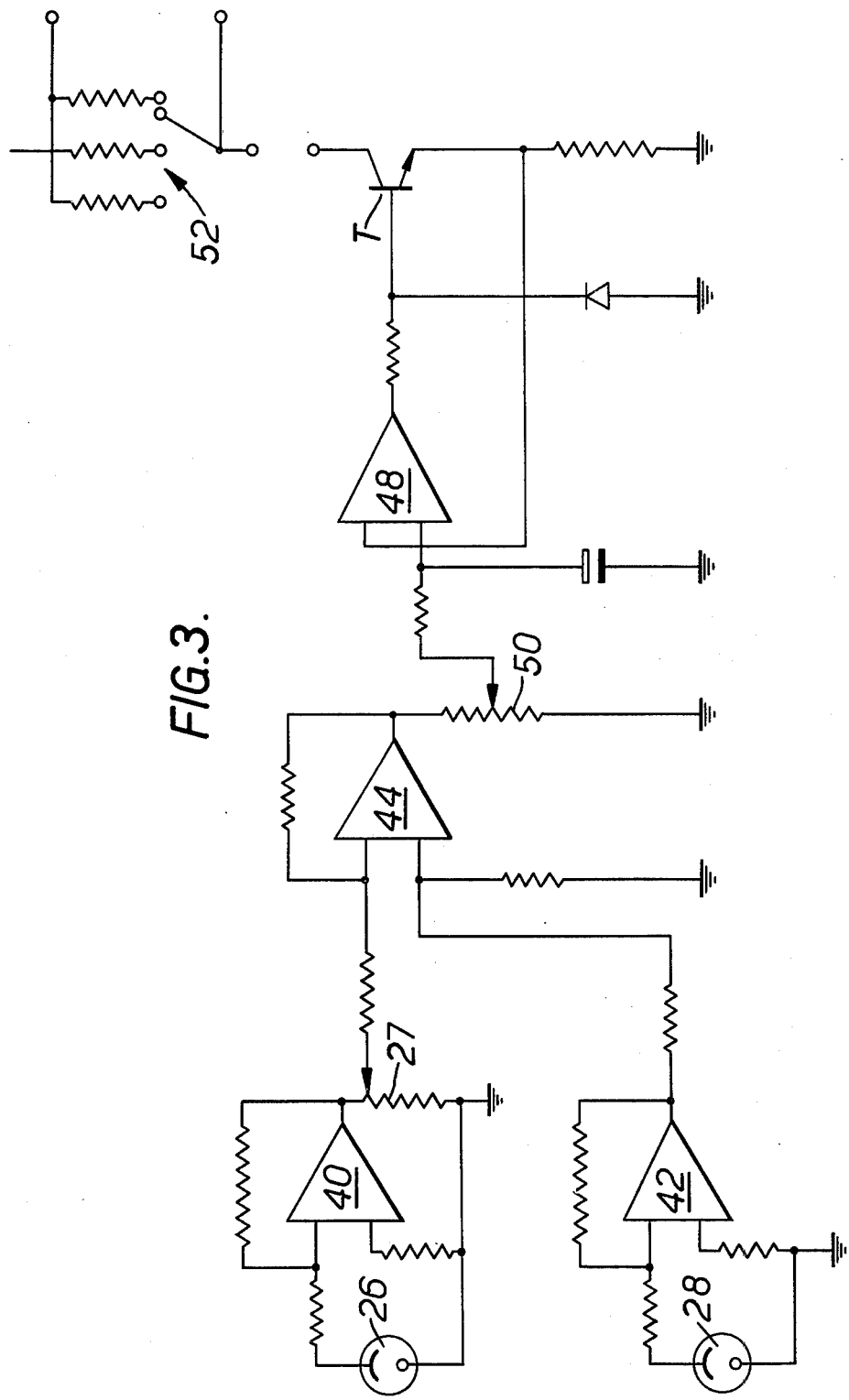

An embodiment of the invention will now be particularly described by way of example with reference to the accompanying drawings in which:

FIG. 1 is a schematic drawing of a glass absorption and titration cell used for assessing sulphur dioxide in air by the method of the invention, FIG. 2 is a schematic drawing of the optical system including the titration cell of FIG. 2, and FIG. 3 is a schematic diagram of a circuit for controlling the titration current through the cell of FIG. 1.

Referring to FIG. 1 of the drawing apparatus for monitoring the sulphur dioxide content of air includes a combined absorption and titration cell indicated generally at 2. The cell 2 comprises a container 4 which retains the liquid to be brought into contact with the air and which includes diametrically opposed optical flats 3, 3' or other transparent opening effective to provide an optical transmission path through the liquid.

An outlet tube 6 connectable to a suction pump (not shown), passes through a closure 8 for the container 4 and is effective in use to draw air through the liquid by way of an inlet tube 10. Inlet tube 10 also passes through the closure 8 and terminates below the indicated level of liquid in container 4.

Also passing through closure 8 is a cylinder 12 which houses a silver anode 11 separated from the main volume of liquid in container 4 by way of a semi-permeable membrane 14 in the form of an agar plug supported on a sintered glass disc. A cathode in the form of a platinum wire 16 extends into the liquid through a suitable glass-to-metal seal provided at the upper end of inlet 10.

In use and as shown generally in FIG. 2, the cell 2 is disposed with its optical path aligned with a light source 20, a collimating arrangement comprising spaced lenses 22 and an optical filter 23. Light from the lamp source 20 passing through the optical system including cell 2, is arranged for incidence upon a photoelectric cell 26 the output of which is indirectly balanced with the output of a second photoelectric cell 28. Cell 28 is arranged to receive light directly from the lamp 20 by way of a glass plate 29 aperture 30 and a filter 32 having optical characteristics matched to those of filter 23.

The optical system as a whole is enclosed in a housing which is indicated generally at 34 and which is effective to protect the photo cells 26, 28 from spurious externally-generated light liable to degrade accuracy of measurement. Substantially light-tight inlet and outlet openings 36 and 38 are provided in the housing 34 to permit air flow to cool the lamp 20. Since lamp 20 is common to both light beams respectively terminating in cells 26, 28 errors arising from variation in light output are considerably reduced.

As shown in FIG. 3, the outputs of photoelectric cells 26 and 28 respectively are applied to the inputs of amplifiers 40 and 42. The outputs of amplifiers 40, 42 are balanced at the input of amplifier 44 which is arranged to produce a zero output at the required light input to cell 26. The balance point is adjustable by the variable gain control comprising potentiometer 27 shunting the output selected point of amplifier 40.

The output signal from amplifier 44 now representative of an out-of-balance condition between cells 26 and 28, is applied to a further amplifier 48 by way of a second variable gain control 50. Amplifier 48 controls the output of power transistor T supplying titration current between the anode and cathode of the titration cell 2 of FIG. 1. The titration current through the cell 2 is also applied for display to a recorder by way of resistance network 52.

In operation of the instrument, the container 4 together with the anode compartment 12 are filled to the levels indicated, with a water-based liquid containing hydrogen peroxide, methyl orange and sodium chloride in selected concentrations.

The quiescent pH of the liquid is selected to lie between 3.9 and 4.0 by the initial addition of hydrochloric acid. At this pH, the colour density of the methyl orange is at the selected datum from which the greatest colour change, consistent with least interference from carbon dioxide, is produced for a given increment of dissolved sulphur dioxide. The potentiometer 46 is accordingly pre-set to provide a "balance" output from amplifier 48 which is effective to bias power transistor T to cut off and reduce titration current through the liquid to zero.

For assessment of the sulphur dioxide content of air, the pump connected to the outlet tube 6 is activated and draws air through the water so that sulphur dioxide selectively dissolved is oxidised to sulphuric acid by the hydrogen peroxide.

Any increase in sulphuric acid concentration produces a colour change in the methyl orange from the datum and an out-of-balance condition in the outputs of the photoelectric cells 26, 28. The titration current produced between cathode 16 and anode 11 in response to the out-of-balance signal from amplifier 44 is effective to electrolyse the sodium chloride to sodium hydroxide and chlorine. Sodium hydroxide continues to be produced until the balance condition between the photoelectric cells 26, 28 is restored at the pH level selected as the datum. Chlorine evolved at the anode is restrained in the anode compartment 12 and is unable to affect the titration balancing process. For safety, evolved chlorine reacts with the silver of the anode to produce an inert chloride which is stable and can be subsequently removed.

The instantaneous titration current produced between the cathode 16 and the anode 11 accordingly is representative of the sulphuric acid produced and thereby is indicative of instantaneous sulphur dioxide concentration in the air drawn through the cell 2. The sulphur dioxide concentration can be directly displayed and assessed on an appropriately calibrated recorder connected across resistance network 52.

In a typical instrument the titration cell has a diameter of about 38 mm providing a typical path gap of 5 mm between electrodes 11 and 16. The volume of solution provided in a typical cell is conveniently about 25 ml so as to be able to cope with an airflow rate of some 500 ml per minute.

The foregoing parameters are suitable for monitoring the sulphur dioxide content of air in a works environment. A more sensitive arrangement for use in urban environments where sulphur dioxide levels are normally lower can be obtained, for example, by increasing the cell diameter to some 53 mm providing an optical path gap of 15 mm. Improved sensitivity is also obtained by increasing the air flow rate to 1,000 milliliters per minute and increasing the volume of solution to 50 ml to sustain substantially the same operating period. Further improvement in sensitivity can be obtained by the use of bromocresol green as an indicator.

It will be appreciated that while the invention has been described with reference to assessing the sulphur dioxide content of air it can equally be applied to the assessment of other toxic gases such as carbon monoxide. In this case the liquid in container 4 comprises a solution prepared by adding to dimethylformamide, a solution of potassium iodide and ethamolamine. Preferably the solution which contains an indicator made up of 0.1% w/v of thymolphthalein in dimethylformamide, is constituted of 780 ml of dimethylformamide added to 20 ml of the indicator, a solution of 30g of potassium iodide in 30 ml of water and 30 ml of ethanolamine.

In its balanced condition the indicator gives the solution a blue colour which makes the use of filters such as Ilford filter No. 607 preferably at 23, 32 in the apparatus of FIG. 2.

In use, air contaminated by carbon monoxide is initially treated to remove any carbon dioxide by passing the air at a selected flow rate through a series of absorption tubes. The absorption tubes respectively contain in sequence a self-indicating silica gel to remove moisture, soda asbestos of about 14 to 20 mesh to remove carbon dioxide, magnesium perchlorate to remove the small amount of moisture produced during the soda asbestos/carbon dioxide reaction molecular sieve to remove hydrocarbons and Schutzes reagent. The Schutzes reagent which is essentially iodine pentoxide converts the carbon monoxide remaining to carbon dioxide which is titrated by the solution in cell 4.

The carbon dioxide in the air offered for titration tends to make the indicator colourless, a tendency which is neutralised by the electrolytic current through electrodes 11 and 16 brought by an out-of-balance condition between photoelectric cells 26 and 28 as a result of indicator colour changes. While the reaction produced by absorption of carbon dioxide into the solution in cell 4 and by the titration current is not fully understood the following are believed to occur:

$$KI \rightarrow K^+ + I^- \tag{1}$$

$$K^+ + e \rightarrow K \tag{2}$$

$$I^- \rightarrow \tfrac{1}{2}I_2 + e \tag{3}$$

$$K + HOCH_2CH_2NH_2 \rightarrow KOCH_2CH_2NH_2 + \tfrac{1}{2}H_2 \tag{4}$$

-continued $$CO_2 + 2HOCH_2CH_2NH_2 \longrightarrow \begin{array}{c} HOCH_2CH_2-NH \\ | \\ C=O \\ | \\ O^- \\ | \\ HOCH_2CH_2-NH_3^+ \end{array} \quad (5)$$

$$\begin{array}{c} HOCH_2CH_2-NH \\ | \\ C=O \\ | \\ O^- \\ | \\ HOCH_2CH_2-NH_3^+ \end{array} + KOCH_2CH_2NH_2$$

$$\begin{array}{c} H \\ | \\ HOCH_2CH_2-N-C-OK \\ \| \\ O \end{array} \quad (6) \swarrow \searrow \quad NH_2CH_2CH_2-O-C-OK \quad (7)$$

$$+2HOCH_2CH_2NH_2 \qquad +2HOCH_2CH_2NH_2$$

In reaction (4) the potassium liberated at the cathode is believed to react with monothanolamine to form the base necessary to retain balance in the solution.

It will be appreciated that while this embodiment has been described with reference to the determination of carbon monoxide in air it can equally be adapted to measure the carbon dioxide content by omitting the initial step of absorption of carbon dioxide in the tube containing soda asbestos.

We claim:

1. A method for monitoring the toxic constituent of an ambient gas comprising bringing the gas into contact with a liquid having one component in which the toxic constituent is selectively soluble together with an indicator having optical transmission characteristics responsive to the quantity of constituent in solution, passing an electric current continuously representative of a change in transmission characteristic from a datum value through a second component which electrolyses so as to tend to neutralise solution changes in said liquid arising from dissolved toxic constituent and thereby restore the transmission characteristics of the indicator to the datum value.

2. A method as claimed in claim 1 wherein the electrolytic current is passed through the liquid by way of electrodes, the volume surrounding one electrode being separated from the remainder of the liquid by a semi-permeable membrane.

3. A method as claimed in claim 2 wherein the electrode within the separated volumes is of a material capable of combining with the electrolytic product generated within that volume.

4. A method as claimed in claim 1, wherein the magnitude of the electric current is displayed as an indication of constituent concentration.

5. A method as claimed in claim 4 wherein the second component is sodium chloride and the anode volume is separated from the remainder of the liquid by a semi-permeable membrane.

6. A method as claimed in claim 5 wherein the anode is of silver.

7. A method as claimed in claim 1 wherein a change in transmission characteristics is detected by detecting the attenuation of a light beam passed through the liquid.

8. A method as claimed in claim 7, wherein an optical transmission filter is interposed in the light beam.

9. A method as claimed in claim 7 wherein the attenuated beam is compared with an unattenuated beam derived from a common light source.

10. A method as claimed in claim 9 wherein the beams are respectively incident upon individual photo electric devices and a difference signal derived from the devices is used to control the electrolytic current.

11. A method as claimed in claim 10 wherein the electrolytic current is provided by an amplifier responsive to the difference signals derived from the photoelectric devices.

12. A method as claimed in claim 1 wherein the carbon monoxide constituent of air is monitored by selectively removing carbon dioxide and converting residual carbon monoxide to carbon dioxide which is selectively dissolved in the liquid.

13. A method as claimed in claim 12 wherein the liquid comprises an aqueous solution of potassium iodide, ethanolamine and dimethylformamide.

14. A method as claimed in claim 12 wherein the indicator is a solution of thymolphthalein in dimethylformamide.

15. A method as claimed in claim 12 wherein the carbon dioxide is removed by bringing the air into contact with soda asbestos.

16. A method as claimed in claim 15 wherein residual carbon monoxide is converted by contact with a form of iodine pentoxide.

17. A method as claimed in claim 1 wherein the sulphur dioxide constituent of air is monitored by bringing the air into contact with water.

18. A method as claimed in claim 17 wherein the water contains an oxidising agent effective to convert dissolved sulphur dioxide to sulphuric acid.

19. A method as claimed in claim 17 wherein the indicator is pH responsive.

20. A method as claimed in claim 19 wherein the indicator is selected from the group consisting of methyl orange and bromocresol green.

21. A method as claimed in claim 17 wherein the water is maintained at a pH datum within the range 3.9 to 4.0.

22. A method as claimed in claim 21 wherein the pH datum is stabilised by hydrochloric acid.

* * * * *